(12) United States Patent
Cremien et al.

(10) Patent No.: US 10,471,421 B2
(45) Date of Patent: Nov. 12, 2019

(54) DEVICE AND METHOD FOR SAMPLING AND DISPENSING A BIOLOGICAL FLUID USING A CAPILLARY TUBE, AND BIOLOGICAL ANALYSIS APPARATUS

(71) Applicant: HORIBA ABX SAS, Montpellier (FR)

(72) Inventors: Didier Cremien, Juvignac (FR); Damien Isebe, Montpellier (FR)

(73) Assignee: HORIBA ABX SAS, Montpellier (FR)

( * ) Notice: Subject to any disclaimer, the term of this patent is extended or adjusted under 35 U.S.C. 154(b) by 438 days.

(21) Appl. No.: 14/905,779

(22) PCT Filed: Jul. 17, 2014

(86) PCT No.: PCT/EP2014/065412
§ 371 (c)(1),
(2) Date: Jan. 15, 2016

(87) PCT Pub. No.: WO2015/007853
PCT Pub. Date: Jan. 22, 2015

(65) Prior Publication Data
US 2016/0151776 A1    Jun. 2, 2016

(30) Foreign Application Priority Data

Jul. 17, 2013    (FR) ..................... 13 57026

(51) Int. Cl.
*B01L 3/02*    (2006.01)
*A61B 5/15*    (2006.01)
(Continued)

(52) U.S. Cl.
CPC .......... *B01L 3/022* (2013.01); *A61B 5/15003* (2013.01); *A61B 5/150022* (2013.01);
(Continued)

(58) Field of Classification Search
None
See application file for complete search history.

(56) References Cited

U.S. PATENT DOCUMENTS 4,133,304 A * 1/1979 Bailey ............... A61B 5/15003
600/577
5,638,828 A    6/1997 Lauks et al.
(Continued)

FOREIGN PATENT DOCUMENTS

FR    2774765 A1    8/1999
JP    2003-159235 A    6/2003
(Continued)

OTHER PUBLICATIONS

International Search Report issued in International Patent Application No. PCT/EP2014/065412 dated Aug. 26, 2014.

*Primary Examiner* — Benjamin R Whatley
(74) *Attorney, Agent, or Firm* — Arent Fox LLP

(57) ABSTRACT

The present application relates to: (i) a sampler device for taking a sample of biological fluid, which comprises a capillary component, and a base rigidly connected to said capillary component and provided with a first connector capable of being reversibly attached in a leaktight manner to a second connector of a dispensing device; (ii) a dispensing device which also comprises means for transferring diluting fluid which open into said second connector. The application also relates to a biological analysis apparatus implementing the sampler and dispensing devices and to a method for sampling and dispensing a biological fluid.

17 Claims, 5 Drawing Sheets

Figure 1:
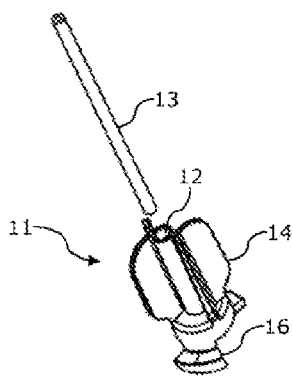

(51) Int. Cl.
*A61B 5/157* (2006.01)
*G01N 35/10* (2006.01)

(52) U.S. Cl.
CPC ...... *A61B 5/150343* (2013.01); *B01L 3/0293* (2013.01); *A61B 5/157* (2013.01); *A61B 5/150755* (2013.01); *B01L 2200/027* (2013.01); *B01L 2300/0838* (2013.01); *G01N 35/1095* (2013.01); *G01N 2035/1034* (2013.01)

(56) References Cited

U.S. PATENT DOCUMENTS

| | | | |
|---|---|---|---|
| 6,284,548 B1 | 9/2001 | Berndtsson | |
| 2013/0142709 A1* | 6/2013 | Lin ........................ | G01N 27/26 422/538 |
| 2016/0245793 A1* | 8/2016 | Samsoondar ...... | A61B 5/14539 |

FOREIGN PATENT DOCUMENTS

| WO | WO 03/044488 A1 | 5/2003 |
|---|---|---|
| WO | WO 01/75416 A1 | 10/2011 |

* cited by examiner

DEVICE AND METHOD FOR SAMPLING AND DISPENSING A BIOLOGICAL FLUID USING A CAPILLARY TUBE, AND BIOLOGICAL ANALYSIS APPARATUS

CROSS-REFERENCE TO RELATED APPLICATION(S)

This application is a 35 U.S.C. 371 National Phase of PCT Application Serial No. PCT/EP2014/065412 filed Jul. 17, 2014, which claims priority to French Application Serial No. 1357026, the disclosure of these prior applications are hereby incorporated by their entirety by reference.

TECHNICAL FIELD

The present invention relates to a device for sampling and dispensing a biological sample for biological analysis apparatuses.

The field of the invention is more particularly, but not exclusively, that of biological analysis systems, especially that of blood analysis systems.

PRIOR ART

Blood samples for biological analysis operations are traditionally collected by puncturing a vein.

Venous sampling requires a specific protocol performed by a qualified sample collector or nurse. This technique requires the sampling of a considerable quantity of blood (about 4 ml) from the patient. The blood sample is collected in a conventional tube.

To carry out the analyses, the tube is then introduced into a blood analyzer. A sampling needle is introduced into the tube in order to transfer a certain volume of the collected blood to a sampling system situated inside the analyzer.

The sampling system is in general formed by a sampling valve or by a syringe. It must permit the isolation or precise sampling of a blood aliquot of a predefined volume, which is used for the analysis.

Generally, the volume of blood actually used for the analysis is of the order of a few microliters. It is thus very small by comparison with the several milliliters taken from the patient.

Under certain conditions, venous sampling may prove difficult or even unfeasible. This may in particular be the case with children, or with certain individuals suffering from particular medical conditions (the obese, the elderly, victims of third-degree burns, etc.). In addition, for cultural reasons, it is sometimes necessary to minimize the volumes that are collected.

To address this type of problem, micro-sampling techniques have been developed.

Techniques for collecting samples of blood from capillary vessels are known in particular, which permit a reduction in the quantity of blood collected and make the sampling procedure easier. The blood from the capillary vessels is taken from a small puncture or a small superficial incision made, for example, on a finger tip, or on the sole of the foot in the case of neonates, or else on the earlobe.

The quantity of blood collected may be greatly reduced with this type of technique, but several approaches co-exist.

In some cases, the volume of blood collected may be sufficient, for example of the order of 200 µl, to be able to be harvested in a tube of the kind used for traditional venous sampling or in a mini-tube. The sample may therefore be transferred directly to the sampling system of the blood analyzer (such as the Micros Care ST® from Horiba Medical), via the sampling needle, in order to isolate the volume used for the analyses. In this case, the analyzer functions exactly as in the case of a venous sample collected in a tube.

In other cases, the volume of blood taken from the patient is very small, being the size of a droplet, that is to say of the order of 20 µl to 50 µl. In this case, the volume of the capillary blood sample is too small to be harvested and directly collected by the sampling system of the analyzer in a traditional tube. The volume of blood is then collected with the aid of a capillary or micro-capillary tube: the end of the capillary or micro-capillary tube is placed in contact with the blood droplet, and the blood fills the tube by capillary action.

In general, however, the volume of blood collected is still greater than the volume actually used for the analyses, and this necessitates further sampling of this volume prior to the analysis.

The patent document FR 2 774 765 in particular discloses a system for treating a blood sample that has been collected in a micro-capillary tube. The capillary tube containing the collected sample is introduced into a fluid conduit of the analyzer via an adapter. The blood sample thus finds itself connected to a hydraulic circuit, which is able to direct the sample toward a first pre-dilution container. Once the pre-dilution has been effected, the mixture is directed to the sampling system in order to determine exactly the volume that is necessary for the analysis.

The pre-dilution is made indispensable by the fact that the sampling valve used to extract the volume needed for the analysis requires a volume of liquid much greater than the volume of the micro-sampling.

The system is therefore complex, it uses up more blood than is necessary for the analysis, and, in addition, it involves hazardous manipulations of the capillary tube between the sampling of the blood and its insertion into an adapter.

The document JP 4807587 is also known, which discloses a system by which the volume of blood collected with a micro-capillary can be transferred directly to a sampling system, which permits isolation of the volume needed for the analysis. The micro-capillary tube used to collect the blood sample is inserted into an adapter. This adapter is placed in contact manually with the sampling needle of the analyzer. The volume needed for the analyses is then aspirated by the needle.

However, the sampling of the blood in the capillary tube is dependent on the correct positioning (without air admission) in which the operator holds the micro-capillary with respect to the needle. Indeed, if the contact between the capillary, via its adapter, and the needle is not leaktight, the sampling system will aspirate air and not the blood contained in the capillary.

In addition, the risks of contamination are not inconsiderable.

It is an object of the present invention to make available a device for sampling and dispensing biological samples by which it is possible to minimize the collected sample volumes and to better utilize these collected volumes.

Another object of the present invention is to make available a device for sampling and dispensing biological samples by which it is possible to minimize the manipulations of the sample and of the dilutions.

Another object of the present invention is to make available a device for sampling and dispensing biological samples by which it is possible to reliably collect precise volumes of samples.

Another object of the present invention is to make available a device for sampling and dispensing biological samples by which it is possible to simplify the manipulations that an operator has to perform between the collection of the sample from a patient and its transfer to an analysis system.

DISCLOSURE OF THE INVENTION

This aim is achieved with a sampler device for collecting a sample of biological fluid, characterized in that it comprises:
- a capillary component capable of collecting a sample of biological fluid by capillary action,
- a base rigidly connected to said capillary component and provided with a first connector capable of being reversibly attached in a leaktight manner to a second connector of a dispensing device, so as to create a fluid connection between said capillary component and said dispensing device.

According to some embodiments, the capillary component and the base can be rigidly connected or made in one piece.

According to some embodiments, the sampler device can comprise a capillary tube and a base which is provided with a receiving means capable of receiving an end of said capillary tube and of keeping same leaktight.

In this case, the capillary component, which is a capillary tube, and the base can be separate elements that are joined together.

The sampler device can additionally comprise a fluid connection which connects the capillary component or the receiving means of a capillary tube and the first connector, in such a way as to allow a fluid connection to be established between the component or the capillary tube and the dispensing device.

This means of fluid connection can in particular comprise:
- a fluid channel, which is rectilinear or bent,
- walls of the base integral with the capillary component or with the means for receiving a capillary tube, which walls extend as far as the first connector, for example in the form of an opening extending through the base.

According to some embodiments, the sampler device can comprise:
- a first connector capable of being locked in a second connector by means of a movement comprising a rotation;
- a first connector capable of being locked in a second connector by means of a snap-fit action;
- a first connector comprising a bayonet-type locking system;
- a first connector comprising a thread.

The invention also relates to a device for dispensing biological fluid, which device comprises:
- a second connector capable of being reversibly attached in a leaktight manner to a first connector of a sampler device according to the invention,
- means which serve for transferring transfer fluid and which open into said second connector.

The transfer fluid can comprise, for example, a dilution fluid or a reagent.

The second connector can additionally comprise pressure means and/or spring means which are able to exert a pressure on the first connector when it is inserted into the second connector, so as to ensure the leaktightness of the connection.

The means for transferring transfer fluid can in particular comprise a fluid conduit and/or a tube.

According to some embodiments, the dispensing device can additionally comprise injection means capable of pushing a predefined volume of transfer fluid through the means for transferring transfer fluid in the direction of the second connector.

The injection means can comprise a syringe.

According to some embodiments, the dispensing device can additionally comprise a measuring container arranged in such a way as to be able to directly receive fluid issuing from a capillary component of a sampler device attached to the second connector.

According to some embodiments, the dispensing device can additionally comprise displacement means capable of positioning the second connector:
- in a first position, in such a way as to allow a sampler device to be attached to and removed from said second connector,
- in a second position, in such a way that a transfer fluid issuing from a sampler device inserted in said second connector is able to flow into the measuring container.

The displacement means can comprise:
- means of rotation,
- means of translation.

According to another embodiment of the invention, a miniaturized dispensing device is proposed that can comprise a measuring container and a first receptacle.

Advantageously, the portable dispensing device according to this alternative embodiment can comprise injection means that are capable of pushing the liquid contained in said first receptacle exclusively through the fluid conduit and the capillary component. In this way, the risk of contamination of the blood sample is minimal.

Advantageously, the measuring container according to this alternative embodiment can further comprise means of optical and/or electrical analysis of the liquid that it contains.

According to another alternative of this embodiment, the miniaturized dispensing device can additionally have an interfacing means capable of connecting the miniaturized dispensing device at least mechanically to another analysis device.

Advantageously, the interfacing means according to this alternative embodiment can additionally comprise a fluid connection.

According to another aspect, a device for sampling and dispensing a biological fluid is proposed which comprises a dispensing device according to the invention and at least one sampler device according to the invention.

According to another aspect, an apparatus for analysis of biological fluids is proposed which comprises a dispensing device for biological fluid according to the invention.

The apparatus for analysis of biological fluids can additionally comprise at least one sampler device according to the invention.

Generally, the biological fluids or liquids for which the invention can be used can include bodily fluids such as blood, serum, plasma, saliva, urine, cerebrospinal fluid, or tissue extracts such as bone marrow.

According to some embodiments, the apparatus according to the invention can be intended to analyze a biological fluid that comprises blood.

According to some embodiments, the apparatus according to the invention can additionally comprise a sampling needle and branching means capable of transferring transfer fluid either to said sampling needle or to the dispensing device.

The sampling needle allows a sample of a biological fluid to be collected in a conventional open or closed tube. Thus, the apparatus can be suitable for measuring samples located either in conventional tubes or in capillary tubes.

According to another aspect, a method for sampling and dispensing a biological fluid is proposed, said method using a sampler device, provided with a capillary component, and a dispensing device, said method comprising a step of transfer and dilution of a sample of biological fluid contained in said capillary component by injecting a predefined volume of transfer fluid through the means for transferring transfer fluid and through said capillary component.

According to some embodiments, the sampling and dispensing method according to the invention can comprise:
 a step of transferring the sample of biological fluid and a defined volume of transfer fluid into a measuring container, in such a way as to obtain, in said measuring container, a dilution of the biological fluid that is directly adapted to a biological analysis operation;
 a preliminary step of collecting a sample of biological fluid by capillary action in a capillary component of a sampler device according to the invention.

According to some embodiments, the sampling and dispensing method according to the invention can be implemented with a biological fluid that comprises blood.

It can comprise a step of transferring a defined volume of transfer fluid suitable for obtaining a dilution directly adapted to at least one of the following biological analysis operations:
 counting of cells (such as red blood cells, white blood cells, immature cells, etc.)
 counting of formed elements,
 dosing of an analyte present in the biological fluid,
 cell characterization.

DESCRIPTION OF THE FIGURES AND EMBODIMENTS

Figure 2:
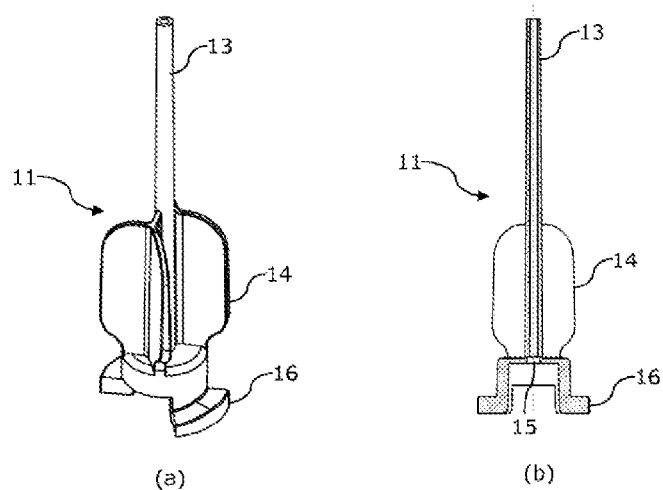
Figure 3:
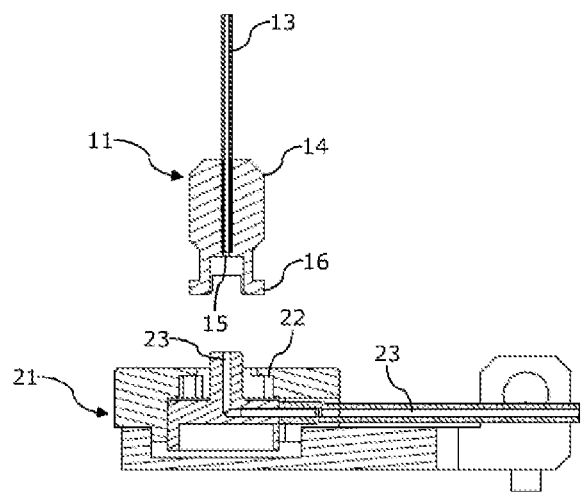
Figure 4:
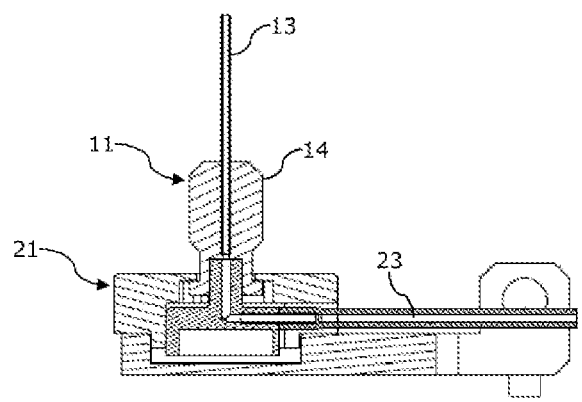
Figure 5:
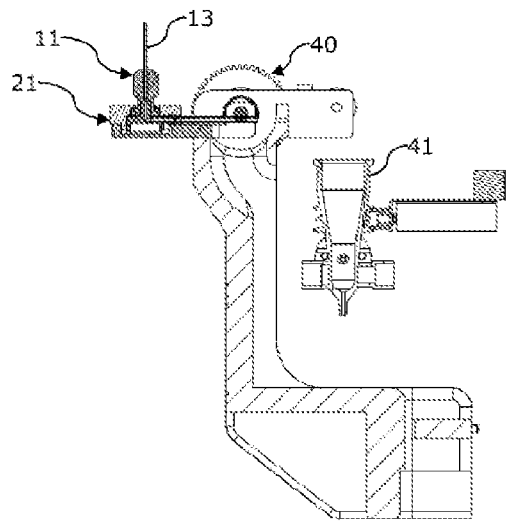
Figure 6:
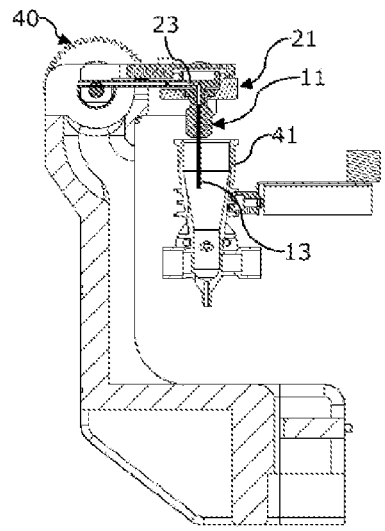
Figure 7:
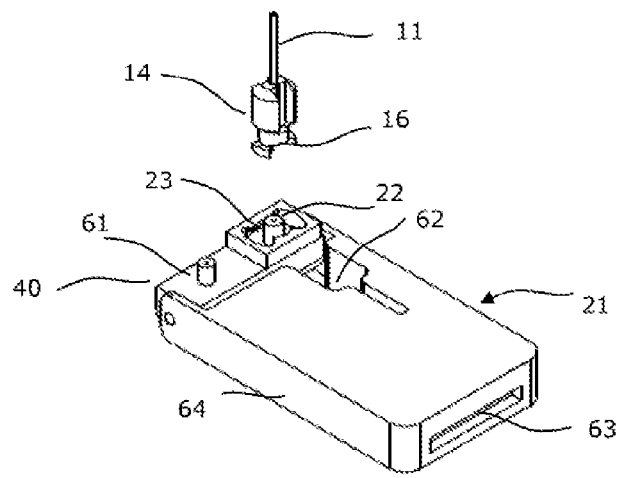
Figure 8:
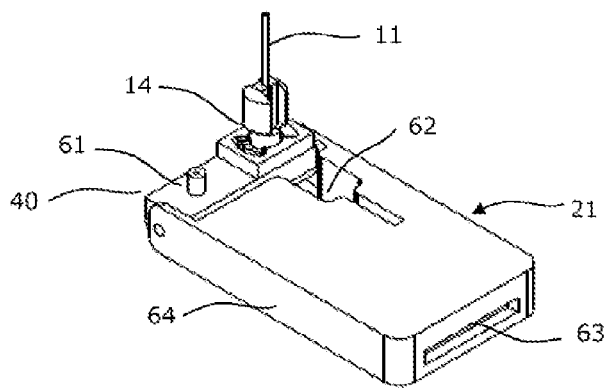
Figure 9:
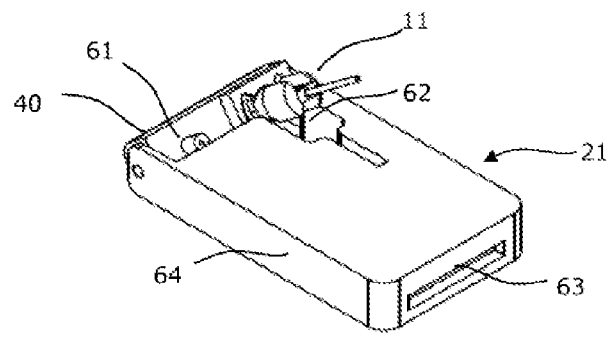
Figure 10:
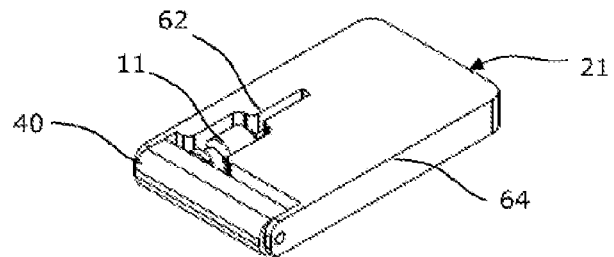
Figure 11:
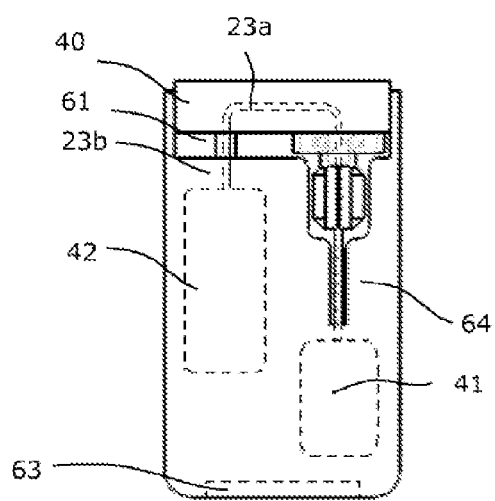

Other advantages and particular features of the invention will become clear on reading the detailed description of uses and of embodiments, which are in no way limiting, and of the following appended drawings:

FIG. 1 illustrates a first embodiment of a sampler device according to the invention, FIG. 2 illustrates a second embodiment of a sampler device according to the invention, with FIG. 2(*a*) showing a perspective view and FIG. 2(*b*) showing a sectional view, FIG. 3 illustrates a sampler device and a dispensing device according to the invention, these being disconnected from each other, FIG. 4 illustrates a sampler device and a dispensing device according to the invention, these being attached to each other, FIG. 5 illustrates an apparatus according to the invention, with the dispensing device in a position permitting the attachment and the removal of a sampler device, FIG. 6 illustrates an apparatus according to the invention, with the dispensing device in a position with the sampler device facing the measuring container, FIG. 7 illustrates a miniaturized dispensing device according to another embodiment of the invention, with a sampler device in proximity, FIG. 8 illustrates a sampler device coupled to a miniaturized dispensing device according to the invention, FIG. 9 illustrates a miniaturized dispensing device according to the invention in which the sampler device is in the process of being moved, FIG. 10 illustrates the miniaturized dispensing device according to the invention containing the sampler device in its dispensing position, FIG. 11 illustrates a front view, partially in section, according to FIG. 10.

Embodiments of devices according to the invention will now be described which are intended to be used in blood analysis apparatuses.

As has been explained above, the invention mainly comprises a sampler device and a dispensing device that is capable of receiving the sampler device.

With reference to FIG. 1 and FIG. 2, we will first describe two embodiments (equivalent in terms of function) of the sampler device 11.

According to a first embodiment shown in FIG. 1, the sampler device 11 comprises a microcapillary tube 13 or capillary tube 13. This capillary tube 13 comprises an internal conduit which is dimensioned in such a way that a biological fluid (for example blood) can be introduced into it by capillary action so as to fill it.

The capillary tube 13 is preferably made of a transparent material through which it is possible to verify the presence of blood on the inside. It can be made of glass or plastic, for example. The inner walls of the capillary tube can be treated specifically in accordance with the sampled biological fluid. For example, an anticoagulant can be deposited in the case of collecting a blood sample.

The sampler device 11 likewise comprises a base 14. This base 14 comprises a receiving means 12 or a receptacle 12 intended to receive the end of the capillary tube 13, in such a way as to hold the latter in place and ensure the leaktightness of the connection.

The base 14 likewise comprises a first connector 16 intended to attach the sampler device 11, reversibly and in a leaktight manner, to a second connector 22 of a dispensing device 21, as will be explained in detail below.

The base 14 also comprises a fluid connection 15 in the form of a continuous opening which opens into the first connector 16 and which is situated in the continuation of the receptacle 12 and of the capillary tube 13.

The base 14 can be made, for example, of a molded and/or machined plastic or polymer. It can be provided with raised areas or wings, as illustrated in FIG. 1, to make it easier to grip and manipulate.

According to a second embodiment, shown in FIG. 2, the sampler device 11 comprises a capillary component 13 and a base 14 which are made in one piece (or integrally).

The capillary component 13 comprises an internal conduit which is dimensioned in such a way that a biological fluid (for example blood) can be introduced into it by capillary action so as to fill it.

The base 14 likewise comprises a first connector 16 intended to attach the sampler device 11, reversibly and in a leaktight manner, to a second connector 22 of a dispensing device 21.

The base 14 also comprises a fluid connection 15 in the form of a continuous opening which opens into the first connector 16 and which is situated in the continuation of the internal conduit of the capillary component 13.

The capillary component 13 and the base 14 can be made, for example, from one piece of molded and/or machined plastic or polymer.

This piece can be provided with raised areas or wings in the area of the base 14, as illustrated in FIG. 2, to make it easier to grip and manipulate.

The capillary component 13 can be of any external shape. In the embodiment shown in FIG. 2, its external shape is that of a tube. Thus, without loss of generality, it will also be referred to below as a "capillary tube 13".

In the two embodiments shown, the sampler device 11 with its capillary tube 13 constitutes a micro-sampling device for biological fluid and one which can be used directly for a capillary puncture, for example. Indeed, when the end of the capillary tube 13 is placed in contact with a drop of biological fluid (blood for example), the biological fluid rises by capillary action through the tube 13 until it fills the latter.

According to an advantageous aspect of the invention, the capillary tube 13 is dimensioned such that its internal volume defines a precise volume of sample, for example 10 microliters.

With reference to FIG. 3 and FIG. 4, we will now describe the dispensing device 21 according to the invention.

This dispensing device 21 corresponds to the input interface of a blood analyzer. Its function is to receive sampler devices 11 (produced, for example, according to one or other of the two embodiments shown) with blood samples and to transfer these samples into analysis means of the blood analyzer.

It comprises a second connector 22 intended to receive the first connector 16 of the sampler device 11, as has been explained above.

The first connector 16 comprises lugs that are provided to engage in seats of the second connector 22, in such a way that, by rotation through a quarter of a turn, the sampler device 11 can be attached to the dispensing device 21, as illustrated in FIG. 3. A system of springs (not shown in the figures) ensures that a constant pressure is maintained in order to guarantee the leaktightness of the connection.

The dispensing device 21 likewise comprises a fluid conduit 23 which opens into the second connector 22, in such a way as to establish a fluid connection with the capillary tube 13 through the base 14 when a sampler device 11 is connected. Advantageously, the capillary tube 13 does not touch the fluid conduit 23 when the base 14 is attached to the connector 22, by virtue of the presence of an air space in the fluid connection 15.

Referring to FIG. 5 and FIG. 6, the dispensing device 21 likewise comprises a measuring vessel 41.

According to an advantageous aspect of the invention, this measuring vessel 41 is intended to directly receive the blood sample collected in the capillary tube 13 and a volume of dilution liquid by which it is possible to obtain, in this vessel 41, the dilution or the mixture necessary for the measuring operations: for example a dilution of 1/300 for counting white blood cells or a dilution of 1/15000 for counting red blood cells.

To carry out these measurements, the measuring vessel 41 is connected, for example, to a device for optical or resistance measurements or for flow cytometry measurement, according to techniques well known to those skilled in the art.

To transfer the blood sample and the dilution liquid into the measuring vessel 41, the capillary tube is positioned opposite this measuring vessel 41 according to the configuration in FIG. 6.

Dilution liquid is injected into the conduit 23 of the dispensing device 21, in the direction of the capillary tube 13. This dilution liquid firstly expels the blood sample from the capillary tube 13 into the measuring vessel 41, and it then flows through the capillary tube 13 into this measuring vessel 41.

A dosing system, for example a syringe, is used to inject a predefined quantity of dilution liquid into the conduit 23 and thus into the measuring vessel 41, in such a way as to achieve a precise rate of dilution in this measuring vessel 41 (the volume of blood sample contained in the capillary tube 13 being known).

The homogeneity of the solution in the measuring vessel 41 is ensured by an agitation system, for example by circulation of gas bubbles (bubbling).

Thus, according to advantageous aspects of the invention:

The blood sample is transferred directly from the capillary tube 13, which has been used for collecting it, into the measuring vessel 41 without passing through an internal conduit of the system. The risks of contamination are thus minimized;

The totality of the blood sample can be effectively used for the measurements, without losses. Indeed, all the cells of the blood sample can be counted, for example by having the totality of the diluted solution in the measuring vessel 41 pass into the analysis system. It is thus possible to sample and use very small quantities of blood;

The control of the dilution can be very precise, since one is certain of transferring the totality of the sample contained in the capillary tube 13 into the measuring vessel 41;

The manipulation of the samples by an operator is simple and without risk, since the sampler device 11 can be used directly to collect the sample from someone and is then fitted on the connector 22 of the dispensing device 21. The manipulations are thereby minimized and simplified to the greatest extent. In addition, the capillary tube 13 and its base 14 are positioned and blocked on the dispensing device 21, and, for this reason, the connection to the instrument is independent of the skill of an operator. Indeed, the base 14 is centered on the dispensing device 21 and is maintained in contact by the spring system and the quarter-turn lock in such a way as to ensure a constant pressure and good leaktightness between the capillary 13, via its base 14, and the dispensing system 21.

It will also be noted that sampler devices 11 can be supplied in the form of disposable sampling devices which are brought to the blood analyzer after sampling in order to perform the measurements.

To make the manipulations easier, the dispensing device comprises displacement means 40 in the form of a rotary system 40 as illustrated in FIG. 5 and FIG. 6. The displacement can be manual or motorized.

The dispensing device 21 can thus move between two positions:
a charging position, illustrated in FIG. 5, allowing the sampler device 11 to be placed on and removed from the connector 22 of the dispensing device 21, and
a dispensing position, illustrated in FIG. 6, in which the sampler device 11 is positioned opposite or in line with the measuring vessel 41.

Insofar as the rotation movement takes place in a plane perpendicular to the façade of the blood analyzer, the charging position corresponds to a position external to the apparatus, whereas the dispensing position corresponds to a position internal to the apparatus.

Referring to FIGS. 7 to 11, another embodiment of the present invention is described. This specific embodiment addresses the problem of improving medical diagnostics and the management of patients. It concerns a "point-of-care" approach for which the sampling operations and analyses are performed and interpreted as near as possible to the patient rather than in a central laboratory, so as to be able to take a clinical decision as quickly as possible. To do this, it is essential that blood samples can be collected, conditioned and transported in a reliable and efficient manner. The specific embodiment of the present invention addresses this technical problem and entails a portable dispensing device 21 which is capable, on the one hand, of receiving a sampler device 11 with blood samples and, on the other hand, of transferring said samples into a measuring vessel 41.

A portable dispensing device is understood as a device that is capable of being easily manipulated and transported by an operator. For example, the external dimensions can be slightly greater than those of the sampler device in order to be able to contain the latter entirely. By way of example, dimensions of the order of 5×8×1 cm may be considered for a weight of the order of about one hundred grams. Advantageously, the dimensions of the portable dispensing device are such that it can be easily held in one hand. These sizes are given as examples in order to illustrate the portability of this embodiment of the invention and, as such, they do not constitute a limitation of the claimed scope of the invention.

The portable dispensing device 21 comprises in particular:
second connectors 22 intended to receive the first connectors 16 of the sampler device 11, so as to create a leaktight and reversible connection between the sampler device 11 and the portable dispensing device 21,
a fluid conduit 23 opening into the second connectors 22 and allowing a fluid connection to be established with the capillary tube 13 via the base 14 of the sampler device 11. The fluid conduit 23 comprises a first part 23a situated through the displacement means 40, and a second part 23b situated in the body 64 of the portable dispensing device 21,
displacement means 40 capable of positioning the connector in a first position called the charging position, in which it is possible to attach or remove the sampler device 11 (FIG. 8), and in a second position, called the dispensing position, in which a fluid connection is established between the portable dispensing device 21 and the sampler device 11 (FIG. 10),
a fluid connector 61,
a first receptacle 42,
a second receptacle 41.

According to this alternative embodiment, the portable dispensing device 21 additionally has a seat 62 in the body 64. The seat 62 is capable of receiving at least part of the sampler device 11. When the displacement means 40 are actuated, manually or automatically, the sampler device is moved into said seat 62. In the case illustrated in FIGS. 8 to 10, the displacement means 40 consist of means of rotation.

When the portable dispensing device 21 is in the dispensing position illustrated in FIGS. 10 and 11, the sampler device 11 is connected in a leaktight manner to the fluid conduit 23 of the portable dispensing device 21. The fluid connector 61 ensures the connection between the fluid conduit portion 23a, which is located in the displacement means 40, and the portion 23b, which is integrated in the body 64 of the portable dispensing device 21. The connection is sure to be leaktight at least when the portable dispensing device 21 is in the dispensing position. The fluid connector can be of any form without limitation of the present invention. In the example illustrated in FIGS. 7 to 10, the fluid connector 61 has the form of a stub into the inside of which the fluid conduit 23 opens. According to another embodiment, the fluid connector can have the form of a rotary joint situated at the interface between the displacement means 40 and the body 64 of the portable dispensing device 21.

Moreover, in this dispensing position, the sampler device 11 is at least partially housed in the body 64 of the miniaturized dispensing device 21, in order to protect it, for example, from the external environment and from possible damage during the analyses.

The miniaturized dispensing device 21 additionally has an interfacing means 63 by which the miniaturized dispensing device 21 can be connected at least mechanically to another analysis device. According to another embodiment, this connection can be electronic and/or can include a fluid connection.

FIG. 11 illustrates a partially sectioned view of the miniaturized dispensing device 21 when the sampler device is in the dispensing position. The fluid conduit 23 thus makes it possible to connect the sampler device 21 to a first receptacle 42 and also to a second receptacle 41.

The first receptacle 42 may, for example, contain a diluent or a transfer liquid; it can include injection means for causing a fluid to circulate through the fluid conduit 23.

The second receptacle 41 consists of a measuring container into which are poured the mixture formed by the liquid contained in the first receptacle 42 and the blood sample contained in the capillary 13 of the sampler device 21. The second receptacle can include means for measuring and/or analyzing the mixture thus formed.

Of course, the invention is not limited to the examples that have been described, and many modifications can be made to these examples without departing from the scope of the invention.

The invention claimed is:

1. A device capable of collecting biological fluid comprising:
a capillary component having a first end, a second end, and an internal conduit extending therebetween, wherein the capillary component is capable of collecting a sample of biological fluid by capillary action at the first end;
a dispensing device;
a base rigidly connected to the second end of the capillary component and comprising a first connector reversibly attached in a leak tight manner to a second connector of the dispensing device, so as to create a fluid connection between the internal conduit of the capillary component and a transferring conduit of the dispensing device, wherein the fluid connection is formed via an opening at the base between the second end and the second connector, and wherein the transferring conduit is in fluid communication with and is capable of transferring transfer fluid into the internal conduit of the capillary component via the interface between the first connector and the second connector;
an injector for pushing a predefined volume of transfer fluid through the transferring conduit and into the internal conduit of the capillary component;
a measuring container connected to and capable of directly receiving fluid from the internal conduit of the capillary component that is attached to the second connector; and
a displacement portion operatively connected to and capable of moving the second connector:
in a first position, that allows the capillary component and base to be attached to and removed from the second connector, wherein the first end extends away from the measuring container, and in a second position, that allows the transfer fluid issuing from the internal conduit of the capillary component inserted onto the second connector to flow into the measuring container, wherein the first end extends towards the measuring container.

2. The device of claim 1, wherein the capillary component comprises a tube and the base comprises a receiving portion capable of receiving an end of the capillary tube for maintaining leak tight seal.

3. The device of claim 1, wherein the first connector is configured to be rotatably lockable with the second connector.

4. The device of claim 1, wherein the injector comprises a syringe.

5. The device of claim 1, wherein the displacement portion operates by rotation of the second connector.

6. The device of claim 1, further comprising:
a first receptacle capable of fluid communication with the transferring conduit; and
a measuring container capable of fluid communication with the first receptacle and the transferring conduit via the internal conduit of the capillary component, wherein the device is portable.

7. The device of claim 6, wherein the first receptacle comprises the injector, and wherein the injector is capable of pushing the transfer fluid into the first receptacle exclusively through the transferring conduit and the internal conduit of the capillary component.

8. The device of claim 6, further comprising an interface capable of connecting the portable device at least mechanically to another analysis device.

9. The device of claim 1, wherein the device comprises an apparatus for analysis of biological fluids that is capable of analyzing the biological fluids collected via the capillary component.

10. The apparatus of claim 9, wherein the apparatus for analysis of biological fluids is capable of analyzing blood collected via the capillary component.

11. A method for sampling and dispensing a biological fluid comprising transferring and diluting a sample of biological fluid into the internal conduit of the capillary component of the device of claim 2 by injecting a predefined volume of transfer fluid through the injector for transferring transfer fluid through the internal conduit of the capillary component.

12. The method of claim 11, further comprising transferring the sample of biological fluid and a defined volume of transfer fluid into a measuring container that is in fluid communication with the internal conduit, to dilute the biological fluid for analysis.

13. The method of claim 11, further comprising collecting a sample of the biological fluid through the internal conduit of the capillary component of the device.

14. The method of claim 11, wherein the biological fluid comprises blood.

15. The method of claim 14, further comprising transferring a defined volume of the transfer fluid suitable for obtaining a dilution to perform an analysis of:
counting of cells,
counting of formed elements,
dosing of an analyte present in the biological fluid, cell characterization, or
a combination thereof.

16. The device of claim 1,
wherein when the base is reversibly attached to the second connecter of the dispensing device, the second end of the capillary component forms a seal with the second connector to create the fluid communication between the second end of the capillary component and the transferring conduit at the second connector of the dispensing device.

17. A sampling device for collecting a sample of biological fluid comprising:
a dispensing device;
a tube-shaped capillary component having an internal conduit extending between a first end and a second end thereof;
a base portion at a first end of the capillary component, the base portion further comprising; a first connector having lugs reversibly engaged with seats of a second connector of the dispensing device;
an opening portion in fluid communication with the internal conduit of the capillary component, wherein the opening is between the lugs of the first connector and is configured to sealingly engage with a fluid conduit at the second connector of the dispensing device to form a continuous fluid path from the first end of the internal conduit of the tube-shaped capillary component to the fluid conduit of the dispensing device;
a measuring container connected to and capable of directly receiving fluid from the internal conduit of the capillary component that is attached to the second connector; and
a displacement portion operatively connected to and capable of moving the second connector:
in a first position, that allows the capillary component and base to be attached to and removed from the second connector, wherein the first end extends away from the measuring container, and
in a second position, that allows the transfer fluid issuing from the internal conduit of the capillary component inserted onto the second connector to flow into the measuring container, wherein the first end extends towards the measuring container.

* * * * *